(12) United States Patent
Liu

(10) Patent No.: US 7,094,286 B2
(45) Date of Patent: Aug. 22, 2006

(54) INORGANIC BONE ADHESION AGENT AND ITS USE IN HUMAN HARD TISSUE REPAIR

(75) Inventor: Changsheng Liu, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 10/468,648

(22) PCT Filed: Feb. 26, 2001

(86) PCT No.: PCT/CN01/00282

§ 371 (c)(1),
(2), (4) Date: Oct. 24, 2003

(87) PCT Pub. No.: WO02/066090

PCT Pub. Date: Aug. 29, 2002

(65) Prior Publication Data

US 2004/0086573 A1    May 6, 2004

(30) Foreign Application Priority Data

Feb. 22, 2001  (CN)  ................................ 01 1 05373

(51) Int. Cl.
*A61L 24/02*    (2006.01)
(52) U.S. Cl. .................. 106/690; 106/691; 623/23.62; 623/923; 424/601; 424/602; 424/719; 128/898; 604/500
(58) Field of Classification Search .................. 106/35, 106/690; 623/23.62
See application file for complete search history.

(56) References Cited

U.S. PATENT DOCUMENTS

| | | | | |
|---|---|---|---|---|
| 5,605,713 | A | * | 2/1997 | Boltong ........................ 427/2.1 |
| 6,458,423 | B1 | * | 10/2002 | Goodson ..................... 427/403 |
| 6,533,821 | B1 | * | 3/2003 | Lally ........................ 623/23.62 |

FOREIGN PATENT DOCUMENTS

| | | |
|---|---|---|
| DE | 29914313 U1 | 2/2000 |
| DE | 29922585 U1 | 7/2000 |
| WO | WO 2000/07639 A1 | 2/2000 |
| WO | WO 2000/16819 A1 | 3/2000 |
| WO | WO 2000/45867 A1 | 8/2000 |

* cited by examiner

*Primary Examiner*—C. Melissa Koslow
(74) *Attorney, Agent, or Firm*—Birch, Stewart, Kolasch & Birch, LLP

(57) ABSTRACT

The present invention discloses an inorganic bone adhesive and its use in human hard tissue repairs. The inorganic bone adhesive comprises basic compound, phosphate, calcium phosphate bone cement and retarder with the characteristics of rapid hydration rate and high early strength. Inorganic Bone adhesive can be widely used in the artificial joints fixation, screw fixation as well as comminuted fracture fixation. It is a kind of safe and effective adhesive material and beneficial for the fast postoperative recovery. The final hydration reaction products contains the composition of magnesium phosphate, bio-mineral containing ammonium and apatite-like materials, which has excellent biocompatibility and can be gradually absorbed by surrounding tissues after being implanted in vivo, which benefits the in-growth of the new bone.

8 Claims, 2 Drawing Sheets

INORGANIC BONE ADHESION AGENT AND ITS USE IN HUMAN HARD TISSUE REPAIR

Figure 1:
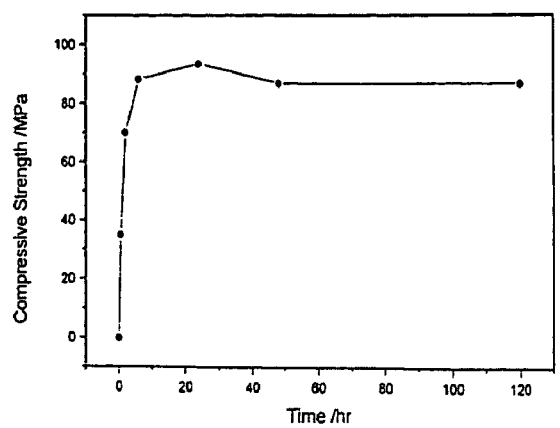

This application is the national phase under 35 U.S.C. § 371 of PCT International Application No. PCT/CN01/00282 which has an International filing date of Feb. 26, 2001, which designated the United States of America.

FIELD OF THE INVENTION

The invention belongs to the field of the biomedical materials, relating to a kind of novel inorganic bone adhesive for human hard tissue repairs, especially involving in the description and use of the inorganic bone adhesive containing phosphates.

BACKGROUND OF THE INVENTION

Fracture by trauma is the common disease in orthopaedics, and the treatment of the unstable fracture (comminuted fracture) is a longstanding problem for the surgeons. At present, the methods of incision restoration with internal fixation have been widely adopted in clinics home and abroad, and the main of which include micro-plates screw fixation, intramedullary fixation, tension wire fixation, introosseous wire suture fixation, intraosseous nylon suture fixation, traditional intersection Kernig needle fixation and absorbable polymeric screw fixation, and so on. These methods have different flaws, which affect the therapeutic effect and functional restoration of the patients. For example, since all of the internal fixation materials are foreign ones, the foreign reactions inevitably occur with different extents. So the second operation is unavoidable in order to take the internal fixation materials out, which certainly brings the patient extra pain and economic burden. The large area of the wound affects the healing of the bone. The operation is a troublesome process with high degree of difficulty. Moreover, the biocompatibility of the implanted materials is bad and the fixed strength is low, especially in the spongy bone areas.

In order to overcome the shortcomings of internal fixation and to solve the problems on the fixation of the small blocks of comminuted fractures, the methods taken in clinics nowadays include the follows:

1. Polymethylmethacrylate (PMMA) Bone Cement

Polymethylmethacrylate (PMMA) bone cement is composed of methylmethacrylate, initiator and some filling materials. The free radical polymerization occurs following the addition of monomer liquid in powder until turning into hard solid. Before setting, the paste can be easily molded and show adhesion. It is usually used for the fixation of artificial joint prosthesis and that of some comminuted fracture (Kerong Dai, Bone and Joint Injuries Magazine, 1995, 10(4): 210–212). But the strong exothermic behavior in the setting reaction will cause the peripheral tissues necrosis. As the main components of organic glasses, PMMA is aged, loosing and falling apart after a long time implantation due to its bad biocompatibility. Its monomer is poisonous and has stimulating smell, which can bring the blood pressure of the patients lower suddenly and even result in the sudden death. When it is used as adhesion, the ratio of long-dated loose and revision of prosthesis is relatively high. The non-degradation characteristic of the materials will keep the fracture from healing and growing for comminuted fracture. In general, the effect of the fixation in comminuted fracture is not very ideal due to the defects of the material itself.

2. For comminuted fracture, fracture reduction is usually adopted, followed by microplates screw fixation (Prevel et al, J-Hand-Surg-Am, 1995; 20(1): 44–49) or intramedullary fixation (Gonzalez et al, Clin-orthop, 1996, 327:47–54), which is effective for the massive bone fracture. It is much difficult to the fixation of the small blocks of bone fracture. In spongy bone areas, moreover, the screw fixation method still has the disadvantage of weak strength, even for the massive bone fracture. The postoperative slippage occurs frequently, which affects the postoperative effects and makes the secondary operation necessary.

Some absorbable internal fixation materials have been developed to eliminate the secondary operation, such as polycaprolactone (Lowry K. J et al., J. Biomed Mater. Res., 1997 36(4): 536–541), and calcium phosphate glass fibre enhanced poly-lactic acid (Slivka M. A et al., J. Biomed. Mater. Res., 36(4): 469–477). But the rapid decline in their mechanical strength limits their applications.

3. For screw fixation, the slippage usually occurs due to the incompact combination between the screw and the spongy bone. The polymer bone cement, such as PMMA, is used to perfuse the bore surrounding the screw in clinics and the screw is fixed after the setting of the cement. Consequently, the fixation strength is enhanced. But it becomes loose and falls apart eventually due to the bad biocompatibility and non-degradation characters of PMMA itself.

4. At present, PMMA is used popularly in the joint fixation and filling of defects after the revision of the prosthesis. (Kuhn K. D. et al., bone cements, Berlin: Springer-Verlag, 2000). Although some improvements on PMMA have been made including the decrease of its heat liberation, the increase of fluidity and injection capacity, some disadvantages still exist, like bad biocompatibility, long-term shedding and higher revision ratios.

For the fixation of the fracture, screw and prosthesis of the joints, all available materials and methods exist disadvantages with different extents. It is desirable to improve their properties, especially biocompatibility, exothermicity and fixation strength.

The magnesium phosphate cement (MPC) is popularly used in the rush repair of the airfield and road, owing to the rapid setting and high early strength characteristics (WO 9721639 AI, 1997). Weill et al., disclosed a kind of calcium phosphate bone cement containing magnesium oxide, soluble phosphate, sand and fly ash, which is used in the rush repairs in constructions (U.S. Pat. No. 4,756,762). Sechra disclosed a fast setting cement used in concrete pavements repairs (Cement Concrete Research 1993, 23: 254–66). All of these have no special requirements to the components and purities of the raw materials, hydration reaction heat, and the toxicity of the materials and additives.

Hirano et al., disclosed the calcium-containing magnesium phosphate cement with the component of $Ca_3Mg_3(PO_4)_4$ and eugenol solvents, which is used for the root canal filling and repair (JP 04352706, 1992). The results indicated that the cement was non-toxic with good biocompatibility. But its hardening process was slow and lasts about 40 min. In particular, the early strength is not high.

Frazier D. D et al, disclosed a kind of poly (propylene glycol-fumarate) bone cement reinforced by particles of calcium carbonate or calcium phosphate. Its early adhesive strength can up to 30 MPa, and its highest compressive strength can reach 300 MPa (J. Biomed. Mater. Res., 1997, 35(3): 383–389). Sakai T. et al., disclosed 4-META/MMA-TBB bone cement filled with hydroxyapatite (HAP) (J. Biomed. Mater. Res., 2000, 52(1): 24–29), which indicated that the incorporation of HAP was beneficial for the poststability of the cement and bone fixation. But the compressive strengths of these two kinds of cements were derived from the polymerization of monomers, rather than the hydration of the inorganic component. Moreover, the materials can't be absorbed after being implanted in vivo, and the foreign materials exist all along. In addition, the heat liberation from polymerization process will burn the peripheral tissues.

SUMMARY OF THE INVENTION

An object of the present invention is to disclose a kind of inorganic bone adhesive with the characteristics of rapid-setting and high early strength. Through the hydration reaction of calcium phosphate or magnesium phosphate bone cement, not by free radical polymerization, the paste turned into the hardening body with certain strength and excellent biocompatibility, which is used in the fixation of the fracture, the fixation and revision of the artificial joint and the reinforcing fixation of the screw. Comparing with PMMA, it can be degraded and be absorbed gradually, which solves the related problems in operations and is beneficial for recovery.

Another object of the present invention is to provide the introduction and application of inorganic bone adhesive in human hard tissues repairs.

DESIGN OF THE INVENTION

1. The hardening body was formed from paste, based on the rapid hydration reaction between magnesia and phosphate. The excellent plasticity and viscosity before hardening contribute to the fixation of the artificial joints, the screws and the fragment bones. Its final fixation strength is dependant upon the strength of the hardening body, the binding strength between the hardening body and the host bone, and that between the hardening body and the joint bolt. Since the reaction is exothermic, it is necessary to control the reaction rate therefore the temperature rise can't exceed 50° C. Enhancing the early strength requires the increase of the reaction rate as far as possible; however, restraining the temperature over the hydration needs the decrease of the reaction rate. Thus the use of retarder in the present invention is suggested.

2. Based on the similar characteristics of the paste transforming to the hardening body under the similar hydration reaction, the early hydration reaction rate of calcium phosphate cement (CPC) should be improved, therefore it can be used in the treatment of the comminuted fracture.

3. Temperature has an obvious influence on the setting rate of calcium phosphate bone cement, but the setting reaction itself is slightly exothermic. With the characteristics of rapid setting, high early compressive strength and exothermic setting process, the exothermic rate of MPC can be adjusted by the hydration activity of the magnesium compound. The incorporation of the MPC into CPC can accelerate the setting of the CPC. The slight expansion of the MPC hardening body during the setting process just makes up the shrinkages of the CPC at that time, which makes the CPC combine closely with the pore wall. This can be used for the fixation of the fracture and artificial joints.

The hydration product of magnesium phosphate bone cement is ammonium magnesium phosphate; a kind of bio-mineral, and the hydration product of calcium phosphate cement is hydroxyapatite. So the present invention has taken the requirements of the high biocompatibility into consideration at the initial design.

DETAILED DESCRIPTION OF THE INVENTION

The mixture of the present invention consists of basic compound, phosphate, retarder and calcium phosphate bone cement.

The basic compound should generally comprise from about 30 to 80 weight percent with the range of about 55 to 65 percent being more preferred.

The phosphate may generally comprise from about 20 to 70 weight percent with the range of about 35 to 45 percent being more preferred.

The retarder may be utilized from about 0.05 to 10 weight percent by weight of basic compound and phosphate. Preferably an amount from 2 to 6 weight percent is utilized.

The amount of calcium phosphate bone cement may comprise from about 0.5 to 20 weight percent by weight of basic compound and phosphate.

The basic compound is magnesium oxide and/or calcium oxide, of which magnesium oxide is preferred.

The phosphates are dihydrogen phosphate, ammonium polyphosphate, and the mixtures derived from them, wherein dihydrogen phosphate includes ammonium dihydrogen phosphate, monocalcium phosphate monohydrate or monocalcium phosphate anhydrous, of which ammonium polyphosphate and ammonium dihydrogen phosphate are preferred.

The retarders are sodium fluorosilicate, sodium polyphosphate, borate, boric acid ester and the mixtures derived from them, of which sodium borate is preferred.

CPC is the mixture of several kinds of calcium phosphates and it can be prepared by the method disclosed in U.S. Pat. No. 5,525,148 and U.S. Pat. No. 5,545,254. It could be the mixture of one or two of tricalcium phosphate ($\alpha$-type or $\beta$-type) and tetracalcium phosphate, and also could be one or the mixture of octacalcium phosphate, calcium dihydrogen phosphate, hydroxyapatite and fluorapatite.

Preparation and Application of the Inorganic Bone Adhesive

Inorganic bone adhesive powder can be obtained by evenly mixing all kinds of raw materials mentioned above according to fixed proportion, of which the basic compound is the dried powder with the diameter range of 1 um~10 um. The setting liquid is added to make the inorganic bone adhesive powder into paste and it can be implanted into the body subsequently. The proportion between inorganic bone adhesive and liquid is from 3:1 to 5:1 (g/ml).

The setting liquid could be saline, redistilled water or the water solution of the additives and regulators. The quantity of liquids is determinated by the standard viscosity measurement method. Since the liquid adopted is different, the fluidity and viscosity of the paste are different; therefore the hydration rate and the early and final strength of the hydration are different.

In order to understand the invention better, the illustration is made further through the characteristic determination in vitro and biocompatibility evaluation of inorganic bone adhesive. And the attached figures show the experimental results.

Methods and Experiments (1) Setting Measurement

Inorganic bone adhesive paste (example 1) was loaded into a stainless-steel mold (6 mmD×12 mmH) with periodic packing by means of stainless-steel rod (5.66 mm in diameter). The force applied to the rod packing was 2 kg to expel air as far as possible. The paste was shaped like cylinder, then the specimen was removed and put into a glass tube (8 mmD×20 mmH), and then the glass tube was sealed with film and stored at 37° C., 100% relative humidity for some time. Take it out to measure the compressive strength. The load is exerted at a rate of 1 mm/min on a universal testing machine. Each group should contain at least 5 parallel test samples. FIG. 1 indicates that the strength has reached 35 MPa at the point of 0.5 hour and 70 MPa at the point of 1 hour, respectively.

(2) Viscosity Strength Measurement

A. Inorganic bone adhesive paste (example 1) mixed adequately was loaded into the stainless-steel mold (10 mmD×10 mmH) with periodic packing by means of stainless-steel rod (5.6 mm in diameter). The force applied to the rod packing was 2 kg to expel air as far as possible. And then the sample was sealed with film and stored at 37° C., 100% relative humidity for some time. The viscosity strength was calculated through the pressure divided by the contacting area between the material and the stainless steel wall. The load is exerted at a rate of 1 mm/min on a universal testing machine. Each group should contain at least 3 parallel test samples.

B. The bone adjacent the joints was shaped like cylinder and drilled in the center. The surface of the bone is scrubbed and handled. Inorganic bone adhesive paste (example 1) was loaded into the bone cavity (10 mmD×15.7 mmH), and then the sample was stored at 37° C., 100% relative humidity for some time. The viscosity strength was calculated through the pressure divided by the contacting area between the material and the surrounding bone. The load is exerted at a rate of 1 mm/min on a universal testing machine. It can be expressed by the following equations:

$$\sigma_{ch} = \frac{F}{S} = \frac{F}{\pi \cdot D \cdot H}$$

It is indicated that the viscosity strength between the material and the stainless steel has reached 2.67 MPa after setting for 0.5 hour. The maximum viscosity strength is 10.99 MPa over the hydration period.

In order to investigate the viscosity strength between the material and the bone, spongy bone from joints was used to measure the viscosity strength between them. The measuring result is 3.95 MPa. According to the bibliographic report (Kerong Dai, et al., China Trauma Magazine, 1989, 27(5): 309–313), the necessary strength required between the bone cement and the bone interface for the adults with the standard weight is 0.92 MPa, and the viscosity strength between PMMA and bone reaches 2.0 MPa after 24 months (J. Biomed. Mat. Res. 2000, 49(2): 237–88). It shows that the above results can meet the requirements in clinical application.

(3) Adiabatic Measurement

It was well known that human tissue is sensitive to the temperature. High temperature probably results in the unrecovered degeneration of the protein or the death of the bone cell. Even if no infection, it may cause aseptic necrosis postoperation, which would result in the loose and gap between the tissue and materials.

Consequently, heat liberation is another important characteristics for the material. Our purpose is to ensure the rapid setting of the materials, and also to control the exothermicity as far as possible. Just in this way, the heat liberation will do little harm to the peripheral tissues.

A. Inorganic bone adhesive paste (example 1) mixed adequately was loaded into a glass tube. Insert the thermometer quickly and make glass bulb containing mercury in the center. The glass tube was put into the thermos bottle filled with glassy-cotton and the temperature was recorded at various intervals.

B. The test was made according to the methods described in "Surgery implants-acrylic acid bone cement, Appendix C: the measurement of the highest exothermic temperature of the system". The test mold was shown in FIG. 4 and FIG. 5, which was made of polytetrafluoroethylene.

Figure 6:
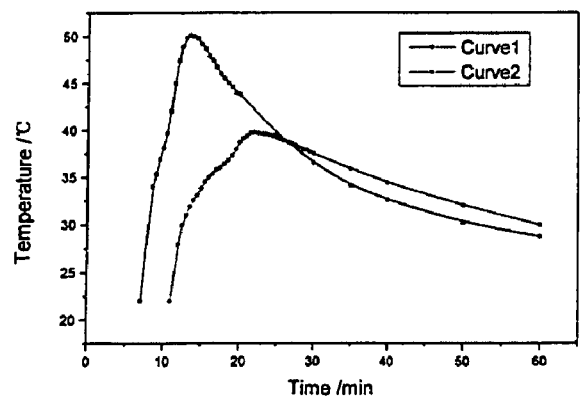

The experiment is carried out at 22° C., 80% relative humidity. Inorganic bone adhesive pastes (Example 1 and Example 2) were quickly loaded into the mold respectively within 1 minute before setting of the material. Insert the thermometer quickly and begin to record the temperature. It was recorded every 30 seconds at the beginning and every 5 or 10 minutes when the variation of the temperature is slight. FIG. 6 showed that the exothermicity of cement was dependant on the amount of acidic component in the system. The curve 1 (Example 1) and curve 2 (Example 2) represent the specimens setting rapidly and slowly, respectively. With the comparison between two curves, the rapid hydration reaction would lead to the sharper exothermic peak and most of the heat is released in a short period and the highest temperature over the hydration can reach 50.1° C. On the contrary, the slow hydration reaction of the system would cause the wider exothermic peak and most of the heat is released in a relative long period, and the highest temperature is only 39.8° C. The temperatures are acceptable to human beings. The setting time and early strength corresponding to the two curves are summarized in the Table 1.

TABLE 1

The relationship among the setting time, the early strength and the highest temperature

|  | Setting time/min | $\sigma_{0.5\,hr}$/MPa | Highest temperature ° C. |
|---|---|---|---|
| Curve 1 | 8.7 | 59.86 | 50.1 |
| Curve 2 | 13.8 | 31.84 | 39.8 |

(4) Biocompatibility

As a kind of biomaterial, inorganic bone adhesive would inevitably contact with the human tissues and bloods. In order to ensure the security of the human and prevent the side reaction in clinical application caused by the material after being implanted into the body, it is necessary to make a complete evaluation for the safety of the material, the biocompatibility of the material, the adhesion behavior between the material and the bone, the stability of the material after the material is implanted into the body.

(4)-1 Toxicity Experiment 25 g of inorganic bone adhesive paste (example 1) were made into 1 mm-thick slices. Quality Detection Center for medical polymer products under State Food & Drug Administration was entrusted to conduct the cytotoxicity test, skin sensitization test, intracutaneous test, and acute systemic toxicity according to GB/T16175—1996 standard. The results are summarized in the table 2.

TABLE 2

The results of the toxicity

| Items | Requirements | Results | Conclusions |
|---|---|---|---|
| Cytotoxicity test | ≦1 grade | Proliferation method: 0 grade | Qualified |
| Skin sensitization test | No | Sensitization rate: 0% | Qualified |
| Intracutaneous test | No | Stimulating index: 0.0 | Qualified |
| Acute systemic toxicity | No | No | Qualified |

The results indicated that all the tests are qualified and the material proves to be non-toxic and would be safe when used into the animal experiment, which laid a solid foundation for the application of the inorganic bone adhesive.

(4)-2 Implant Experiment

A. Preparation of the Standard Implanted Specimen

Inorganic bone adhesive paste (example 1) mixed adequately was loaded into the stainless steel mold (6 mmD×10 mmH) and the mold (3.2 mmD×10 mmH). The force applied was 2 kg to expel air as far as possible and the specimens were sterilized by Co-60 irradiation before being implanted into the body.

B. Animal Implant Experiment 15 rabbits with the weight of 3 kg (provided by Animal Center of Shanghai Secondary Military Medical University) were divided into 5 groups and each group contained 3 ones. The rabbits were made lie on the back and then fixed on the plate. 3% pentobarbital was used in the abdominal injection for narcosis at the dosage of 30 mg/kg. 2 ml of blood was drawn by puncture of vein, and then it was put into the biochemical glass tube marked in advance. The specimen was in static culture for more than 0.5 h, and then temporarily stored in 4° C. refrigerator or sent to be tested in time. The hair at calvarium and front left leg was taken, and then the skin was sterilized by iodine and covered with sterilized towel. A cut on the left-side calvarium was made to cause the exposure of the skull. The periosteum was cut open and lateral bone plate was eliminated to form a bone groove (6 mmD×10 mmH). The MPC (6 mmD×10 mmH) specimens were implanted, and then the soft tissue was sutured closely in delamination. Antibiotics ointment was spread on the cut. The proximal part of the front left leg was bonded with tourniquet. A slitting was made in the outer condyle of the femur. The external condyle was expose and the periosteum was cut open. The internal condyle was expose and the periosteum was cut open by using the same method. A hole was drilled by a 3.2 mm drill in diameter with the horizontal trend of external condyle to internal condyle. The residues were cleaned and the bleeding was stopped with wet sponge. The MPC (3.2 mmD×10 mmH) specimen was loaded into the bone cavitas and then soft tissue was sutured closely in delamination. The tourniquet was unbinded and antibiotics ointment was spread on the cut. 2 ml of blood was drawn postoperatively for biochemical evaluation. X-ray examination was immediately taken postoperatively anteroposterior and lateral, respectively. The rabbits were sent back to the animal house and its lower limbs had no limitation in activities. Each group (3 rabbits) was killed in 0.5 month, 2 months, 3 months, 6 months, 12 months postoperative and the specimens were taken out, respectively. Before taking out of the specimens, 3% pentobarbital was used in the abdominal injection for narcosis at the dosage of 30 mg/kg. 2 ml of blood was drawn by puncture of vein for biochemical examination. X-ray examination was made on the implanted site. The specimens implanted in skull were taken out and the photographs were also taken. Biomechanical measurement was carried out and then XRD analysis was taken. The SEM examination of the cross-section was made.

The specimens in the femur ankle of the front left leg were taken out. The changes in morphology were examined combined with the observation of the growth of the bone at the interface. The formation of fibrous films, the inflammation and necrosis between the implants and surrounding tissues also should be taken into consideration. The photographs of the specimens were taken, and then the specimens were divided into two parts. One part was put into fixation liquid for the microscope examination. The other was put into the special fixation liquid for the SEM examination. The histological evaluation was carried out based on the analysis of the microscopic photographs and SEM micrograph.

C. Biochemical Analysis of Blood 2 ml of blood was drawn from the veins at the ear edge of the rabbit preoperatively and postoperatively, and then used for the biochemical assays. The concentration of serum calcium, serum phosphate was determinated by CX-3 automatic biochemical analysis instrument, while the concentration of serum magnesium was analyzed by VIDEO-22 atomic spectrophotometer.

D. Examination of the Degradation for the Specimens

The specimens implanted in skull were taken out, and then the photographs of the specimens were taken to examine the degradation for the implants.

E. Biomechanics Test

The specimens implanted in skull were taken out and the compressive strengths were measured with the loading rate of 1 mm/min on a universal testing machine.

After inorganic bone adhesive paste (example 1) was implanted for 3 months, the concentration of the serum calcium, the serum phosphate and the serum magnesium remain the normal physiological level and have no apparent differences, except the slight fluctuation in serum phosphate. The results indicated that the implanted material did not cause an obvious change in the animal's metabolism, and the metabolism of the bodies themselves could balance the concentration of the serum calcium, serum phosphate and serum magnesium.

The results of the implant experiments indicated that the biocompatibility of the inorganic bone cement paste (example 1) with the surrounding tissue was good and it has no obvious foreign body reaction, inflammatory reaction and tissue necrosis after the material was implanted into the body. The material can be degraded gradually, which benefit for the replacement of the material and growth for the new bone.

BRIEF ILLUSTRATION OF THE FIGURES

The invention itself, as well as further objects and advantages thereof, will be better understood with the attached drawings, in which:

FIG. 1, the variation of the compressive strength with time

Figure 2:
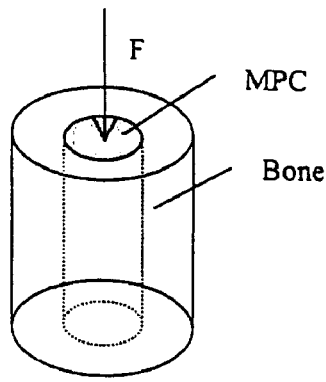

FIG. 2, the mold for the measurement of the viscosity strength

Figure 3:
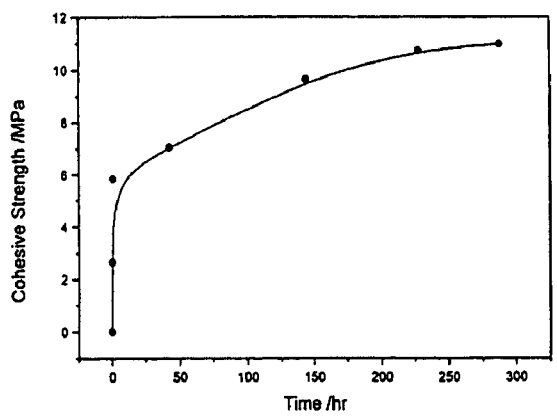

FIG. 3, the variation of the viscosity strength with time

Figure 4:
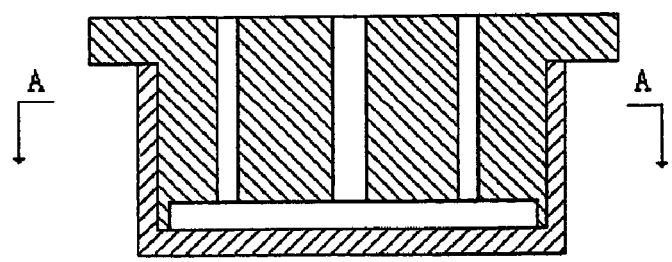

FIG. 4, the mold for measurement of calorimetric behavior

Figure 5:
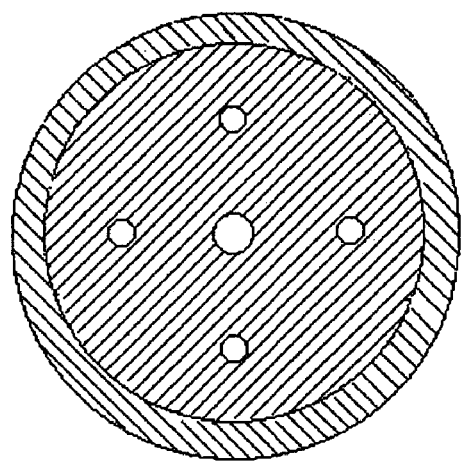

FIG. 5, the diagrams of A—A face of FIG. 4

FIG. 6, adiabatic curves of the inorganic bone adhesive

EXAMPLE 1

The dried reactive MgO powder with the diameter less than 10 μm was mixed with the dried ammonium dihydrogen phosphate by the ratio of 1:1 (weight ratio) to form the inorganic bone adhesive powder with the characteristics of the hydration and adhesion. The powder was then mixed adequately with the retarder by the ratio of 10:0.05 (weight ratio). The powder was then evenly mixed with the saline by the ratio of 4.5:1 (weight/volume) to form the slurry, which subsequently was implanted into the body. When the adhesive was planted in vivo as an inorganic bone adhesive, the method should be followed as described above.

EXAMPLE 2

The dried reactive MgO powder with the diameter less than 10 μm was mixed with the dried ammonium polyphosphate by the ratio of 10:5 (weight ratio) to form the high-active inorganic bone adhesive powder with the characteristics of the hydration and adhesion. The powder was then mixed adequately with the retarder by the ratio of 10:0.5 (weight ratio) or the retarder could also be dissolved in a liquid at the same ratio. The powder could also be mixed adequately by the ratio of 4:1 (weight/volume) with the saline to form the slurry, which subsequently was implanted into the body. When the adhesive was planted in vivo as an inorganic bone adhesive, the method should be followed as described above.

EXAMPLE 3-4

The powder in example 1 or example 2 was mixed with the calcium phosphate bone cement powder by the ration of 10:1 (weight ratio) to form the mixed inorganic bone adhesive. The saline was added into the powder to form the slurry, which subsequently was implanted into the body. When the adhesive was planted in vivo as an inorganic bone adhesive, the method should be followed as described above.

INDUSTRY PRACTICABILITY

From the above, the inorganic bone adhesive in the present invention is a kind of safe and effective cement and has the following advantages.

(1) With the rapid hydration rate and high early strength, it is beneficial for the stability of the fixed site. Especially during the operation, it is favorable for shortening operating time and the fast postoperative healing.

(2) The viscosity of the slurry is good, which is helpful for the adhesion and fixation.

(2) The final hydration products are the bio-minerals and apatite-like, such as ammonium magnesium phosphate. It has no stimulating reaction to the body and is beneficial to maintain the long-term strength owing to good biocompatibility. It even can be absorbed by the organism gradually and be useful to the ingrowth of the new bone.

The invention claimed is:

1. An inorganic bone adhesive comprising about 30–80 weight percent of a basic compound selected from magnesium oxide and/or calcium oxide; about 20 to 70 weight percent of phosphate, selected from the group consisting of ammonium dihydrogen phosphate, monocalcium phosphate monohydrate, monocalcium phosphate anhydrous, ammonium polyphosphate and mixtures derived therefrom; about 0.05 to 10 weight percent of retarder, based on the weight of the basic compound and the phosphate, selected from the group consisting of sodium fluorosilicate, polyphosphate sodium, a borate, boric acid ester and mixtures thereof, and about 0.5 to 20 weight percent of calcium phosphate bone cement, based on the weight of the basic compound and the phosphate.

2. The inorganic bone adhesive of claim 1 wherein said adhesive comprises about 55–65 weight percent of the basic compound; about 35–45 weight percent of the phosphate; about 2–6 weight percent of the retarder based on the weight of basic compound and phosphate; and about 0.5 to 20 weight percent of calcium phosphate bone cement based on the weight of the basic compound and phosphate.

3. The inorganic bone adhesive of claim 1 or claim 2 wherein said basic compound is magnesium oxide.

4. The inorganic bone adhesive of claim 1 or claim 2 wherein said retarder is sodium borate.

5. The inorganic bone adhesive of claim 1 or claim 2 wherein said calcium phosphate bone cement is selected from the group consisting of tricalcium phosphate (a-type or β-type) and tetracalcium phosphate, octacalcium phosphate, calcium dihydrogen phosphate, hydroxyapatite and fluorapatite, and the mixtures derived from them.

6. A process to repair hard tissues of a human or to prepare materials for human bone defect repairs, comprising the steps of:

mixing an adhesive according to claims 1 or 2 with liquid to form a paste; and placing the paste on a surface of said hard tissues or said human bone defect.

7. A process to repair hard tissues of a human or to prepare materials for human bone defect repairs, comprising the steps of:

mixing an adhesive according to claim 3 with liquid to form a paste; and placing the paste on a surface of said hard tissues or said human bone defect.

8. A process to repair hard tissues of a human or to prepare materials for human bone defect repairs, comprising the steps of:

mixing an adhesive according to claim 5 with liquid to form a paste; and placing the paste on a surface of said hard tissues or said human bone defect.

* * * * *